(12) United States Patent
Patel et al.

(10) Patent No.: US 9,884,031 B2
(45) Date of Patent: Feb. 6, 2018

(54) USE OF HDAC INHIBITORS FOR TREATMENT OF CARDIAC RHYTHM DISORDERS

(75) Inventors: Vickas Patel, Havertown, PA (US); Jonathan A. Epstein, Radnor, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 743 days.

(21) Appl. No.: 12/599,480

(22) PCT Filed: May 7, 2008

(86) PCT No.: PCT/US2008/005816
§ 371 (c)(1),
(2), (4) Date: Aug. 11, 2010

(87) PCT Pub. No.: WO2008/140708
PCT Pub. Date: Nov. 20, 2008

(65) Prior Publication Data
US 2010/0298237 A1 Nov. 25, 2010

Related U.S. Application Data

(60) Provisional application No. 60/924,326, filed on May 9, 2007.

(51) Int. Cl.
| | |
|---|---|
| A61K 38/12 | (2006.01) |
| A61K 31/19 | (2006.01) |
| A61K 31/135 | (2006.01) |
| A61P 9/00 | (2006.01) |
| A61K 31/185 | (2006.01) |

(52) U.S. Cl.
CPC .................................. *A61K 31/185* (2013.01)

(58) Field of Classification Search
CPC ................................................... A61K 31/185
See application file for complete search history.

(56) References Cited

U.S. PATENT DOCUMENTS

| | | | |
|---|---|---|---|
| 6,706,686 B2 * | 3/2004 | Long | A61K 31/165 424/9.2 |
| 2006/0199848 A9 | 9/2006 | Fedida et al. | |
| 2006/0276393 A1 * | 12/2006 | Milburn | A61K 31/05 514/183 |
| 2007/0043050 A1 | 2/2007 | Nunes et al. | |
| 2007/0049616 A1 | 3/2007 | Ksander et al. | |
| 2009/0105168 A1 * | 4/2009 | Gruber et al. | 514/43 |

FOREIGN PATENT DOCUMENTS

| | | | | |
|---|---|---|---|---|
| WO | WO 2006060382 A2 * | 6/2006 | | A61K 31/19 |
| WO | WO 2007115287 A2 * | 10/2007 | | A61K 38/00 |

OTHER PUBLICATIONS

Myocardial ischemia from http://mayoclinic.com/health/myocardial-ischemia/DS01179, pp. 1-2. Accessed Oct. 19, 2012.*
Ryohei Furumai, Potent histone deacetylase inhibitors built from trichostatin A and cyclic tetrapeptide antibiotics including trapoxin, PNAS, Jan. 2001, vol. 98, pp. 87-92.*
Hae Jin Kee, Inhibition of Histone Deacetylation Blocks Cardiac Hypertrophy Induced by Angiotensin II Infusion and Aortic Banding, Circulation. 2006;113:51-59; originally published online Dec. 27, 2005.*
New York-Presbyterian Hospital, nyp.org/news/hospital/1089.html, posted online Sep. 12, 2006, accessed on Sep. 18, 2014.*
Manisha H. Shah, Cardiotoxicity of Histone Deacetylase Inhibitor Depsipeptide in Patients withMetastatic Neuroendocrine Tumors, Clin Cancer Res 2006;3997 12(13) Jul. 1, 2006.*
Milos Dokmanovic, Histone Deacetylase Inhibitors: Overview and Perspectives, Mol Cancer Res 2007;5(10). Oct. 2007, pp. 981-990.*
Aldo P. Maggioni, Valsartan Reduces the Incidence of Atrial Fibrillation in Patients With Heart Failure: Results From the Valsartan Heart Failure Trial (Val-HeFT), Am Heart J. 2005;149(4):548-557.*
Hyun Kook, Cardiac hypertrophy and histone deacetylase—dependent transcriptional repression mediated by the atypical homeodomain protein Hop, The Journal of Clinical Investigation | Sep. 2003 | vol. 112 | No. 6 863-871.*
G Y H Lip, BMJ. Jan. 8, 2000; 320(7227): 104-107. PMCID: PMC1117365 ABC of heart failure: Aetiology.*
Hyun Kook, Cardiac hypertrophy and histone deacetylase—dependent transcriptional repression mediated by the atypical homeodomain protein Hop, J. Clin. Invest. 112:863-871 (2003). doi:10.1172/JCI200319137.*
Yongli Kong, Suppression of Class I and II Histone Deacetylases Blunts Pressure-Overload Cardiac Hypertrophy, Circulation. 2006; 113(22): 2579-2588. doi:10.1161/CIRCULATIONAHA.*
Beatriz Mattos, Sudden Death Risk Stratification in Hypertrophic Cardiomyopathy: Genetic and Clinical Bases, 2006, pp. 351-359.*
Ogawa et al. Suberoylanillide Hydroxamic Acid Enhances Gap Junctional Intercellular Communication via Acetylation of Histone Containing Connexin 43 Gene Locus. Cancer Res. 65 (21) Nov. 1, 2005 p. 9771-9778.
Kang J et al "Copper induces histone hypoacetylation through directly inhibiting histone acetyltransferase activity" (Chem Biol Interact. Jul. 20, 2004; 148(3): 115-23.
Liu C et al "Inhibition of histone deacetylases" Methods Mol Biol: 2004; 287: 87-97.
Sefton, "Implantable Pumps", CRC Crit. Ref. Biomed. Eng. 14:201 (1987).
Buchwald et al., "Long-term, continuous intravenous heparin administration by an implantable infusion pump in ambulatory patients with recurrent venous thrombosis" Surgery 88:507 (1980).
Saudek et al., "A preliminary trial of the programmable implantable medication system for insulin delivery", N. Engl. J. Med. 321:574 (1989).
Goodson, "Dental Applications", in Medical Applications of Controlled Release, supra, vol. 2, pp. 115-138 (1984).
Langer, "New Methods of Drug Delivery", Science 249:1527-1533 (1990).

(Continued)

*Primary Examiner* — James H Alstrum-Acevedo
*Assistant Examiner* — Erinne R Dabkowski
(74) *Attorney, Agent, or Firm* — Mark S. Cohen; Pearl Cohen Zedek Latzer Baratz LLP (57) ABSTRACT

The present invention provides methods of ameliorating or reducing the extent of cardiac arrhythmia disorders, by administering an inhibitor of histone deacetylase enzyme (HDAC).

10 Claims, 2 Drawing Sheets

(56) References Cited

OTHER PUBLICATIONS

Pousti et al., "Effect of Sodium Valproate on Ouabain-Induced Arrhythmia in Isolated Guinea-Pig Atria", Iranian Journal of Pharmacology and Therapeutics 2007, vol. 6, No. 1, pp. 41-43.
Levy, "Atrial Fibrillation, the Arrhythmia of the Elderly, Causes and Associated Conditions", Ana Kar Der, 2002;2: 55-60.
Gurvich et al., "Histone Deacetylase Is a Target of Valproic Acid-Mediated Cellular Differentiation", Cancer Research 2004, 64, 1079-1086.
Phiel et al., "Histone Deacetylase Is a Direct Target of Valproic Acid, a Potent Anticonvulsant, Mood Stabilizer, and Teratogen", The Journal of Biological Chemistry, 2001, vol. 276, No. 39, pp. 36734-36741.

* cited by examiner

USE OF HDAC INHIBITORS FOR TREATMENT OF CARDIAC RHYTHM DISORDERS

CROSS-REFERENCE TO RELATED APPLICATIONS

This is a national stage application of PCT patent application PCT/US2008/005816, filed May 7, 2008, that claims the benefit of priority from U.S. Provisional Application 60/924,326, filed May 9, 2007, both of which are incorporated by reference herein in their entirety.

FIELD OF THE INVENTION

The present invention provides methods of ameliorating, treating or reducing the extent of cardiac rhythm disorders, by administering an inhibitor of histone deacetylase enzyme (HDAC).

BACKGROUND OF THE INVENTION

Atrial fibrillation is an irregular, rapid, chaotic heart rhythm disorder that is a chronic and debilitating medical condition. It is the most common cardiac arrhythmia and accounts for one-third of all hospitalizations for cardiac rhythm disorders in the United States. Patients with atrial fibrillation experience increased morbidity including lower exercise tolerance, frequent palpitations and heart failure. Atrial fibrillation is particularly prevalent in patients with heart failure and patients with both diseases are at risk for increased mortality. In particular, left ventricular hypertrophy and diastolic dysfunction are independent risk factors for the development of atrial fibrillation and both are associated with a higher incidence of atrial fibrillation. Antiarrhythmic drug therapy for atrial fibrillation is relatively ineffective for restoring and maintaining sinus rhythm and is associated with multiple side effects. The discovery that ectopic foci arising from the pulmonary veins trigger atrial fibrillation has led to catheter-based pulmonary vein isolation as an effective therapy for atrial fibrillation. Pulmonary vein isolation offers benefits over antiarrhythmic drugs but present techniques are associated with procedural risks and are less efficient in patients with left ventricular hypertrophy.

In the setting of abnormal ventricular function, atrial structural changes such as dilatation and fibrosis are prevalent and promote arrhythmogenesis. Normalization of ventricular function, by inhibiting angiotensin, appears to partially reverse atrial structural changes and reduce atrial arrhythmogenesis. Experimental and clinical evidence support the ability of angiotensin-inhibition to reduce atrial fibrillation, however evidence also exists that angiotensin-independent pathways contribute to atrial structural remodeling and atrial fibrillation.

SUMMARY OF THE INVENTION

The present invention provides, in one embodiment, a method of treating a cardiac rhythm disorder in a subject, comprising administering to a subject an inhibitor of a histone deacetylase (HDAC), thereby treating a cardiac rhythm disorder in a subject.

In another embodiment, the present invention provides a method of reducing the incidence of a cardiac rhythm disorder in a subject, comprising administering to a subject an inhibitor of a histone deacetylase (HDAC), thereby reducing the incidence of a cardiac rhythm disorder in a subject.

In another embodiment, the present invention provides a method of reducing atrial collagen content in a subject, comprising administering to a subject an inhibitor of a histone deacetylase (HDAC), thereby reducing atrial collagen content in a subject.

In another embodiment, the present invention provides a method of reducing the incidence of atrial arrhythmogenesis in a subject, comprising administering to a subject an inhibitor of a histone deacetylase (HDAC), thereby reducing the incidence of atrial arrhythmogenesis in a subject.

BRIEF DESCRIPTION OF THE FIGURES

The foregoing summary, as well as the following detailed description of the invention, will be better understood better when read in conjunction with the appended drawings and tables. It should be understood, however, that the invention is not limited to the precise arrangements and instrumentalities shown.

FIG. 1 shows a micrograph of Mason's trichrome staining of an atrium. Hop transgenic mice ($Hop^{Tg}$) are compared with wild-type controls (WT), and trichostatin A treated Hop transgenic mice (TSA-Hop). Scale Bar: 40× images=1 mm; 400× images=100 µm. The lower panel depicts bar graphs showing atrial fibrosis (left panel) in the $Hop^{Tg}$ group compared with wild-type controls, and trichostatin A Hop transgenic mice (TSA-Hop). *$P<0.05$.

FIG. 2A shows angiotensin II in WT and $Hop^{Tg}$ hearts when assessed by enzyme-linked immunoabsorbent assays. FIG. 2B-F shows the relative protein expression of the activated form of several mitogen-activated protein kinases and cytokines assessed by Western-blot analysis in the atrium of Hop transgenic mice ($Hop^{Tg}$) compared with wild-type controls (WT) and Hop transgenic mice treated with trichostatin A (TSA-Hop). Panel (B) is phospho-JNK (46- and 54-kDa isoforms), panel (C) is phospho-p38-MAPK, panel (D) is phospho-ERK1/2 (42- and 44-kDa isoforms), panel (E) is activated TGF-β1 (25-kDa) and panel (F) is activated IL-1β (28-kDa). Below the blots are normalized band signal intensities to GAPDH (isoforms of ERK and JNK were averaged for quantitative analysis). Blots are representative of three separate experiments. *$P<0.05$ compared to WT; †$P<0.05$ compared to TSA-$Hop^{Tg}$.

FIG. 3A shows immunoblot analysis of atrial connexin40 in wild-type (WT), Hop transgenic (Hop) and trichostatin A-treated Hop transgenic mice (TSA), while FIG. 3B show parallel analysis for atrial connexin43 in wild-type, Hop transgenic and trichostatin A-treated Hop transgenic mice. Blots are representative of three separate experiments. *$P<0.05$ compared to WT; †$P<0.05$ compared to TSA-$Hop^{Tg}$.

DETAILED DESCRIPTION OF THE INVENTION

The present invention provides methods of ameliorating or reducing the extent of cardiac rhythm disorders, by administering an inhibitor of histone deacetylase enzyme (HDAC).

In one embodiment, the present invention provides a method for treating a cardiac rhythm disorder in a subject comprising administering an inhibitor of an HDAC. In another embodiment, the present invention provides a method for ameliorating a cardiac rhythm disorder in a subject comprising administering an inhibitor of an HDAC. In another embodiment, the present invention provides a method for reducing the incidence of a cardiac rhythm disorder in a subject comprising administering an inhibitor of an HDAC.

In another embodiment, the present invention provides a method of treating a cardiac rhythm disorder in a subject, comprising administering to a subject an inhibitor of a histone deacetylase (HDAC), thereby treating a cardiac rhythm disorder in a subject. In another embodiment, the cardiac rhythm disorder comprises an irregular cardiac rhythm. In another embodiment, the cardiac rhythm disorder comprises a rapid cardiac rhythm. In another embodiment, the cardiac rhythm disorder comprises a chaotic cardiac rhythm.

In another embodiment, the present invention provides a method of treating a cardiac arrhythmia. In another embodiment, cardiac arrhythmia of the present invention comprises an irregularity in the force of the heartbeat. In another embodiment, cardiac arrhythmia of the present invention comprises an irregularity in rhythm of the heartbeat. In another embodiment, cardiac arrhythmia of the present invention is a group of conditions in which the muscle contraction of the heart is irregular or is faster or slower than normal.

In another embodiment, the present invention provides that some arrhythmias are life-threatening medical emergencies that can cause cardiac arrest and sudden death. In another embodiment, the present invention provides that arrhythmias cause aggravating symptoms, such as an awareness of a different heart beat, or palpitation, which can be annoying. In another embodiment, the present invention provides that some arrhythmias are benign and normal.

In another embodiment, the present invention comprises sinus arrhythmia. In another embodiment, sinus arrhythmia is the mild acceleration followed by slowing of the normal rhythm that occurs with breathing.

In another embodiment, the present invention provides that arrhythmias that are due to fast, abnormal electrical activity can cause tachycardias that are dangerous. In another embodiment, the present invention provides that if the ventricles of the heart experience one of these tachycardias for a long period of time, there can be deleterious effects. In another embodiment, the present invention provides that individuals sense a tachycardia as a pounding sensation of the heart, known as palpitations. In another embodiment, the present invention provides that if a tachycardia lowers blood pressure it may cause lightheadedness or dizziness, or even fainting (syncope). In another embodiment, the present invention provides that if the tachycardia is too fast, the pump function of the heart is impeded, which may lead to a sudden death.

In another embodiment, the present invention provides that a serious variety of arrhythmia is known as fibrillation. In another embodiment, the present invention provides that fibrillation occurs when the heart muscle begins a quivering motion due to disunity in contractile cell function. In another embodiment, the present invention provides that fibrillation affects the atrium (atrial fibrillation) or the ventricle (ventricular fibrillation). In another embodiment, the present invention provides that ventricular fibrillation is imminently life-threatening.

In another embodiment, the present invention provides that atrial fibrillation is the quivering, chaotic motion in the upper chambers of the heart, known as the atria. In another embodiment, the present invention provides that atrial fibrillation is due to serious underlying medical conditions, and should be evaluated by a physician. In another embodiment, the present invention provides that ventricular fibrillation occurs in the ventricles of the heart; it is always a medical emergency. In another embodiment, the present invention provides that ventricular fibrillation (VF, or V-fib) can lead to death within minutes.

In another embodiment, the present invention provides that arrhythmias are often first detected by simple but nonspecific means: auscultation of the heartbeat with a stethoscope, or feeling for peripheral pulses. In another embodiment, the present invention provides that a specific diagnostic test for assessment of heart rhythm is the electrocardiogram (abbreviated ECG or EKG).

In another embodiment, the present invention further comprises SADS, or sudden arrhythmia death syndrome. In another embodiment, SADS is a term used to describe sudden death due to cardiac arrest brought on by an arrhythmia. In another embodiment, causes of SADS in young people are long QT syndrome, Brugada syndrome, catecholaminergic polymorphic ventricular tachycardia and hypertrophic cardiomyopathy and arrhythmogenic right ventricular dysplasia ("arrhythmia"-causing, "right ventricle"-involving, pre-cancerous malformation (bad-growth)). Each cause of SADS represents a separate embodiment of the present invention.

In another embodiment, the present invention comprises various arrhythmias. In another embodiment, the present invention comprises atrial arrhythmias. In another embodiment, the present invention comprises sinus bradycardia. In another embodiment, the present invention comprises sinus tachycardia. In another embodiment, the present invention comprises atrial fibrillation. In another embodiment, the present invention comprises atrial flutter. In another embodiment, the present invention comprises supraventricular tachycardia. In another embodiment, the present invention comprises premature atrial complex. In another embodiment, the present invention comprises ventricular arrhythmias. In another embodiment, the present invention comprises idioventricular rhythm. In another embodiment, the present invention comprises accelerated idioventricular rhythm. In another embodiment, the present invention comprises ventricular tachycardia. In another embodiment, the present invention comprises ventricular fibrillation. In another embodiment, the present invention comprises premature ventricular complex. In another embodiment, the present invention comprises junctional arrhythmias. In another embodiment, the present invention comprises junctional rhythm. In another embodiment, the present invention comprises junctional tachycardia. In another embodiment, the present invention comprises premature junctional complex. In another embodiment, the present invention comprises heart blocks, also known as AV blocks. In another embodiment, the present invention comprises first degree heart block, also known as PR prolongation. In another embodiment, the present invention comprises second degree heart block. In another embodiment, the present invention comprises Type 1 second degree heart block, also known as Mobitz I or Wenckebach. In another embodiment, the present invention comprises Type 2 second degree heart block, also known as Mobitz II. In another embodiment, the present invention comprises third degree heart block, also known as complete heart block. Each arrhythmia represents a separate embodiment of the present invention.

In another embodiment, the present invention provides a method of treating a cardiac rhythm disorder in a subject, comprising administering to a subject an inhibitor of a histone deacetylase (HDAC), thereby treating a cardiac rhythm disorder in a subject. In another embodiment, the present invention provides a method of reducing the incidence of a cardiac rhythm disorder in a subject, comprising administering to a subject an HDAC inhibitor, thereby reducing the incidence of a cardiac rhythm disorder in a subject. In another embodiment, the present invention provides a method of reducing atrial collagen content in a subject, comprising administering to a subject an HDAC inhibitor, thereby reducing atrial collagen content in a subject. In another embodiment, the present invention provides a method of restoring an atrial connexin distribution in a subject, comprising administering to a subject an HDAC inhibitor, thereby restoring an atrial connexin distribution in a subject. In another embodiment, the present invention provides a method of reducing the incidence of atrial arrhythmogenesis in a subject, comprising administering to a subject an HDAC inhibitor, thereby reducing the incidence of atrial arrhythmogenesis in a subject.

In another embodiment, the subject of the present invention is further affected with a ventricular hypertrophy disorder. In another embodiment, a ventricular hypertrophy disorder of the present invention is a left ventricular hypertrophy (LVH). In another embodiment, LVH is the thickening of the myocardium (muscle) of the left ventricle of the heart. In another embodiment, LVH is referred to as a pathological reaction to cardiovascular disease. In another embodiment, LVH is a marker for disease involving the heart. In another embodiment, LVH can be caused by aortic stenosis, aortic insufficiency, and hypertension.

In another embodiment, the subject of the present invention is further affected with a ventricular hypertrophy disorder. In another embodiment, a ventricular hypertrophy disorder of the present invention is a right ventricular hypertrophy (RVH). In another embodiment, RVH is caused by pulmonary hypertension, tetralogy of fallot, pulmonary valve stenosis, ventricular septal defect (VSD), and high altitude.

In another embodiment, the subject of the present invention is further affected with a diastolic dysfunction. In another embodiment, diastolic dysfunction is caused due to the left ventricle's inability to properly fill with blood during diastole. In another embodiment, in the setting of a stiff left ventricle, it is more difficult for blood to flow into it from the left atrium. In another embodiment, any condition or process that leads to stiffening of the left ventricle can lead to diastolic dysfunction. In another embodiment, left ventricular stiffening is caused by high blood pressure, aortic stenosis, scarred heart muscle, diabetes, severe systolic dysfunction that has led to ventricular dilation. In another embodiment, diastolic dysfunction is caused by mitral stenosis.

In another embodiment, the cardiac rhythm disorder of the present invention is an atrial fibrillation disorder also termed auricular fibrillation. In another embodiment, atrial fibrillation involves a rapid heart rate, in which the atria are stimulated to contract in a very disorganized and abnormal manner. In another embodiment, atrial fibrillation is caused by disruption of the normal functioning of the electrical conduction system of the heart. In another embodiment, the atria are stimulated to contract very quickly and differently from the normal activity originating from the sinoatrial node. In another embodiment, this condition can be caused by impulses which are transmitted to the ventricles in an irregular fashion. In another embodiment, this condition can be caused by impulses failing to be transmitted. In another embodiment, this condition leads to an irregular (and usually fast) pulse in atrial fibrillation.

In another embodiment, atrial fibrillation of the present invention comprises atrial flutter. In another embodiment, in atrial flutter the ventricles beat rapidly, but regularly. In another embodiment, if the atrial fibrillation/flutter is part of a condition called sick sinus syndrome, the sinus node does not work properly, and the heart rate may alternate between slow and fast.

In another embodiment, underlying causes of atrial fibrillation and flutter include dysfunction of the sinus node and a number of heart and lung disorders, including coronary artery disease, rheumatic heart disease, mitral valve disorders, pericarditis, and others. In another embodiment, underlying causes of atrial fibrillation further comprise hyperthyroidism, hypertension, or heavy alcohol consumption. Each cause of atrial fibrillation represents a separate embodiment of the present invention.

In another embodiment, the cardiac rhythm disorder of the present invention can be diagnosed by echocardiogram. In another embodiment, the cardiac rhythm disorder of the present invention can be diagnosed by nuclear imaging tests. In another embodiment, the cardiac rhythm disorder of the present invention can be diagnosed by coronary angiography. In another embodiment, the cardiac rhythm disorder of the present invention can be diagnosed by exercise treadmill ECG. In another embodiment, the cardiac rhythm disorder of the present invention can be diagnosed by electrophysiologic study (EPS). Each method of diagnosis represents a separate embodiment of the present invention.

In another embodiment, treating a cardiac rhythm disorder of the present invention comprises restoring atrial connexin distribution in a subject. In another embodiment, disrupted cardiac connexins alter coordinated electrical activation and conduction through myocardial tissue. In another embodiment, altered distribution of connexins is involved in the pathophysiologic mechanism of atrial fibrillation. In another embodiment, alterations in the tissue distribution or function of cardiac connexins predispose to cardiac arrhythmias.

In another embodiment, treating a cardiac rhythm disorder of the present invention comprises reducing atrial collagen content in a subject. In another embodiment, increased collagen deposition is associated with decreased contractile function, and abnormal systolic and diastolic $Ca^{2+}$ handling. In another embodiment, abnormalities in action potential propagation and $Ca^{2+}$ handling contribute to the initiation of atrial arrhythmias. In another embodiment, atrial fibrosis and collagen deposition contribute to the pathogenesis of atrial fibrillation. In another embodiment, the degree of fibrosis is associated with an increase in the expression of extracellular matrix proteins.

In another embodiment, atrial fibrillation is an irregular, rapid, chaotic heart rhythm disorder that is a chronic and debilitating medical condition. In another embodiment, patients with atrial fibrillation experience increased morbidity including lower exercise tolerance, frequent palpitations and heart failure. In another embodiment, atrial fibrillation is particularly prevalent in patients with heart failure and patients with both diseases are at risk for increased mortality. In another embodiment, left ventricular hypertrophy and diastolic dysfunction are independent risk factors for the development of atrial fibrillation and both are associated with a higher incidence of atrial fibrillation. In another embodiment, anti-arrhythmic drug therapy for atrial fibrillation is relatively ineffective for restoring and maintaining sinus rhythm and is associated with multiple side effects.

In another embodiment, in the setting of abnormal ventricular function, atrial structural changes such as dilatation and fibrosis are prevalent and promote arrhythmogenesis.

In another embodiment, the specific histone-deacetylase inhibitor, trichostatin A (TSA), significantly reduces atrial fibrillation. In another embodiment, the specific histone-deacetylase inhibitor, trichostatin A (TSA), significantly reduces atrial fibrillation inducibility in a mouse model of left ventricular hypertrophy. In another embodiment, cardiac hypertrophy induced by Hop over-expression is associated with myocardial fibrosis and shortening of atrial refractoriness but does not appear to alter local angiotensin II levels. In another embodiment, cardiac hypertrophy is characterized by the absence of increased angiotensin II, TGF-β1 and phosphorylated ERK. In another embodiment, cardiac hypertrophy is characterized by elevated atrial collagen content and elevated fibrosis. In another embodiment, cardiac hypertrophy is characterized by altered connexin distribution. In another embodiment, atrial fibrillation is characterized by elevated atrial collagen content. In another embodiment, atrial fibrillation is characterized by altered connexin distribution.

In another embodiment, the methods of the present invention provide that HDAC inhibitor of the invention reduces atrial collagen content. In another embodiment, the methods of the present invention provide that HDAC inhibitor of the invention reduces fibrosis. In another embodiment, the methods of the present invention provide that HDAC inhibitor of the invention reduces arrhythmogenesis. In another embodiment, the methods of the present invention provide that HDAC inhibitor of the invention restores atrial connexin distribution. In another embodiment, the methods of the present invention provide that HDAC inhibitor of the invention does not affect atrial refractoriness. In another embodiment, the methods of the present invention provide that HDAC inhibitor of the invention does not affect action potential duration. In another embodiment, the methods of the present invention provide that HDAC inhibitor of the invention reduces atrial arrhythmogenesis in the setting of left ventricular hypertrophy by reversing atrial structural remodeling and fibrosis. In another embodiment, the methods of the present invention provide that administering HDAC inhibitor to a subject in need reduces the morbidity of cardiac arrhythmia in a subject. In another embodiment, the methods of the present invention provide that administering HDAC inhibitor to a subject in need reduces the morbidity of atrial fibrillation in a subject.

In another embodiment, the methods of the present invention provide that the HDAC inhibitor of the present invention is TSA. In another embodiment, the methods of the present invention provide that TSA reduces atrial collagen content. In another embodiment, the methods of the present invention provide that TSA reduces fibrosis. In another embodiment, the methods of the present invention provide that TSA reduces arrhythmogenesis. In another embodiment, the methods of the present invention provide that TSA restores atrial connexin distribution. In another embodiment, the methods of the present invention provide that TSA does not affect atrial refractoriness. In another embodiment, the methods of the present invention provide that TSA does not affect action potential duration. In another embodiment, the methods of the present invention provide that TSA reduces atrial arrhythmogenesis in the setting of left ventricular hypertrophy by reversing atrial structural remodeling and fibrosis. In another embodiment, the methods of the present invention provide that administering TSA to a subject in need reduces the morbidity of cardiac arrhythmia in a subject. In another embodiment, the methods of the present invention provide that administering TSA to a subject in need reduces the morbidity of atrial fibrillation in a subject.

In one embodiment, the HDAC inhibitor used in methods of the present invention is valproate. In another embodiment, the HDAC inhibitor is trichostatin. In another embodiment, the HDAC inhibitor is trichostatin A (TSA). In another embodiment, the HDAC inhibitor is Scriptaid. In another embodiment, the HDAC inhibitor is a PXD101. In another embodiment, the HDAC inhibitor is a benzamine.

In another embodiment, the HDAC inhibitor is a short-chain fatty acid. In another embodiment, the short-chain fatty acid is a butyrate. In another embodiment, the short-chain fatty acid is a phenylbutyrate. In another embodiment, the short-chain fatty acid is valproate. In another embodiment, the HDAC inhibitor is valproic acid. In another embodiment, the short-chain fatty acid is any other short-chain fatty acid that exhibits HDAC inhibitory activity. Each short-chain fatty acid represents a separate embodiment of the present invention.

In another embodiment, the HDAC inhibitor is a hydroxamic acid. In one embodiment, the hydroxamic acid is a suberoylanilide hydroxamic acid (SAHA). In another embodiment, the hydroxamic acid is a derivative of a SAHA. In another embodiment, the hydroxamic acid is oxamflatin. In another embodiment, the hydroxamic acid is ABHA. In another embodiment, the hydroxamic acid is pyroxamide. In another embodiment, the hydroxamic acid is a propenamide. In another embodiment, the hydroxamic acid is any other hydroxamic acid that exhibits HDAC inhibitory activity. Each hydroxamic acid represents a separate embodiment of the present invention.

In another embodiment, the HDAC inhibitor is an epoxyketone-containing cyclic tetrapeptide. In one embodiment, the epoxyketone-containing cyclic tetrapeptide is a trapoxin. In another embodiment, the epoxyketone-containing cyclic tetrapeptide is an HC-toxin. In another embodiment, the epoxyketone-containing cyclic tetrapeptide is chlamydocin. In another embodiment, the epoxyketone-containing cyclic tetrapeptide is ABHA. In another embodiment, the epoxyketone-containing cyclic tetrapeptide is pyroxamide. In another embodiment, the epoxyketone-containing cyclic tetrapeptide is a diheteropeptin. In another embodiment, the epoxyketone-containing cyclic tetrapeptide is WF-3161. In another embodiment, the epoxyketone-containing cyclic tetrapeptide is a Cyl-2. In another embodiment, the epoxyketone-containing cyclic tetrapeptide is a Cyl-1. In another embodiment, the epoxyketone-containing cyclic tetrapeptide is any other epoxyketone-containing cyclic tetrapeptide that exhibits HDAC inhibitory activity. Each epoxyketone-containing cyclic tetrapeptide represents a separate embodiment of the present invention.

In another embodiment, the HDAC inhibitor is a non-epoxyketone-containing cyclic tetrapeptide. In one embodiment, the non-epoxyketone-containing cyclic tetrapeptide is FR901228. In another embodiment, the non-epoxyketone-containing cyclic tetrapeptide is an apicidin. In another embodiment, the non-epoxyketone-containing cyclic tetrapeptide is a cyclic-hydroxamic-acid-containing peptide (CHAP). In another embodiment, the non-epoxyketone-containing cyclic tetrapeptide is any other non-epoxyketone-containing cyclic tetrapeptide that exhibits HDAC inhibitory activity. Each non-epoxyketone-containing cyclic tetrapeptide represents a separate embodiment of the present invention.

In another embodiment, the HDAC inhibitor is a benzamide. In one embodiment, the benzamide is MS-275 (MS-27-275). In another embodiment, the benzamide is CI-994. In another embodiment, the non-epoxyketone-containing cyclic tetrapeptide is any other non-epoxyketone-containing cyclic tetrapeptide that exhibits HDAC inhibitory activity. Each non-epoxyketone-containing cyclic tetrapeptide represents a separate embodiment of the present invention.

In another embodiment, the HDAC inhibitor is a depudecin. In another embodiment, the HDAC inhibitor is an organosulfur compound. In another embodiment, the HDAC inhibitor is any other HDAC inhibitor known in the art. Each possibility represents a separate embodiment of the present invention.

In another embodiment, a method of present invention further comprises administering to the subject an additional anti-arrhythmia compound. In another embodiment, the HDAC inhibitor of the present invention and the additional anti-arrhythmia compound are formulated and/or administered as a combination. In another embodiment, the combination of an HDAC inhibitor of the present invention and an additional anti-arrhythmia compound are administered in a single dosage form. In another embodiment, the preferred dose of the additional anti-arrhythmia compound is known to a person of skill in the art. In another embodiment, the preferred dose of the additional anti-arrhythmia compound is set in the 2007 Physicians' Desk Reference® (PDR®).

In another embodiment, the additional anti-arrhythmia compound treats atrial fibrillation. In another embodiment, the HDAC inhibitors of the present invention are administered while treating arrhythmia with electrical cardioversion or intravenous (IV) drugs such as dofetilide, amiodarone, or ibutilide. In another embodiment, additional anti-arrhythmia compounds are selected from but not limited to: beta-blockers, calcium channel blockers, digitalis or other medications (such as anti-arrhythmic drugs). In another embodiment, additional anti-arrhythmia compounds are selected from but not limited to: blood thinners, such as heparin or Coumadin. In another embodiment, additional anti-arrhythmia treatments include a catheter procedure on the atria called radiofrequency ablation. In another embodiment, additional anti-arrhythmia treatments include an atrial pacemaker implanted under the skin to regulate the heart rhythm. In another embodiment, additional anti-arrhythmia compounds are selected from but not limited to: digoxin, atenolol, metoprolol, propranolol, amiodarone, disopyramide, ibutilide, verapamil, diltiazem, sotalol, flecainide, procainamide, quinidine, or propafenone.

In another embodiment of methods of the present invention, the dose of the HDAC inhibitor is within a range of about 0.1-100 mg/day. In another embodiment, the dose is between about 0.5-50 mg/day. In another embodiment, the dose is between about 1-30 mg/day. In another embodiment, the dose is between about 2-20 mg/day. In another embodiment, the dose is between about 4-15 mg/day. In another embodiment, the dose is between about 6-10 mg/day.

In another embodiment, the dose is about 0.1 mg/day. In another embodiment, the dose is about 0.15 mg/day. In another embodiment, the dose is about 0.2 mg/day. In another embodiment, the dose is about 0.3 mg/day. In another embodiment, the dose is about 0.5 mg/day. In another embodiment, the dose is about 1 mg/day. In another embodiment, the dose is about 1.5 mg/day. In another embodiment, the dose is about 2 mg/day. In another embodiment, the dose is about 3 mg/day. In another embodiment, the dose is about 5 mg/day. In another embodiment, the dose is about 7 mg/day. In another embodiment, the dose is about 10 mg/day. In another embodiment, the dose is about 15 mg/day. In another embodiment, the dose is about 20 mg/day. In another embodiment, the dose is about 30 mg/day. In another embodiment, the dose is about 50 mg/day. In another embodiment, the dose is about 70 mg/day. In another embodiment, the dose is about 100 mg/day.

In another embodiment, the dose is about 0.1 mg. In another embodiment, the dose is about 0.15 mg. In another embodiment, the dose is about 0.2 mg. In another embodiment, the dose is about 0.3 mg. In another embodiment, the dose is about 0.5 mg. In another embodiment, the dose is about 1 mg. In another embodiment, the dose is about 1.5 mg. In another embodiment, the dose is about 2 mg. In another embodiment, the dose is about 3 mg. In another embodiment, the dose is about 5 mg. In another embodiment, the dose is about 7 mg. In another embodiment, the dose is about 10 mg. In another embodiment, the dose is about 15 mg. In another embodiment, the dose is about 20 mg. In another embodiment, the dose is about 30 mg. In another embodiment, the dose is about 50 mg. In another embodiment, the dose is about 70 mg. In another embodiment, the dose is about 100 mg. In another embodiment, the dose administered the frequency of administration and the duration of the treatment will vary. In another embodiment, the dose administered the frequency of administration and the duration of the treatment will vary as a function of the condition of the patient and is determined according to standard clinical procedures known to the practitioner skilled in the relevant art. Each dose or range thereof represents a separate embodiment of the present invention.

"Treating" a disease or disorder refers, in one embodiment, to arresting the development of the disease or disorder. In another embodiment, "treating" refers to reversing the development of the disease or disorder. In another embodiment, "treating" refers to slowing the development of the disease or disorder. In another embodiment, "treating" refers to alleviating at least one symptom of the disease or disorder. Each possibility represents a separate embodiment of the present invention.

In one embodiment, an active compound of a method of the present invention is administered systemically. In another embodiment, the compound is administered locally.

The pharmaceutical composition comprising an HDAC inhibitor of the invention, in one embodiment, administered to a subject by any method known to a person skilled in the art, such as parenterally, paracancerally, transmucosally, transdermally, intramuscularly, intravenously, intradermally, subcutaneously, intraperitonealy, intraventricularly, intracranially, intravaginally or intratumorally.

In another embodiment, the subject of the present invention is a human subject in need of the methods of the present invention. In another embodiment, the subject of the present invention is an animal in need of the methods of the present invention. In another embodiment, the subject of the present invention is a test animal wherein the methods of the present invention are applied to.

In another embodiment, the pharmaceutical compositions are administered orally, and thus are formulated in a form suitable for oral administration, i.e. as a solid or a liquid preparation. Suitable solid oral formulations include, for example, tablets, capsules, pills, granules, pellets and the like. Suitable liquid oral formulations include solutions, suspensions, dispersions, emulsions, oils and the like. In another embodiment of the present invention, the HDAC inhibitor is formulated in a capsule. In accordance with this embodiment, the compositions of the present invention comprise, in addition to the HDAC inhibitor an inert carrier or diluent, and/or a hard gelating capsule.

In another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

In another embodiment, the pharmaceutical compositions are administered topically to body surfaces, and thus are formulated in a form suitable for topical administration. Suitable topical formulations include gels, ointments, creams, lotions, drops and the like. For topical administration, the HDAC inhibitor of the present invention and its physiologically tolerated derivatives such as salts, esters, N-oxides, and the like is prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of the HDAC inhibitor over a period of time.

Pharmaceutically acceptable carriers or diluents are well known to those skilled in the art. The carrier or diluent is, in one embodiment, a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, and dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In another embodiment, the compositions further comprise binders (e.g. acacia, cornstarch, gelatin, carbomer, ethyl cellulose, guar gum, hydroxypropyl cellulose, hydroxypropyl methyl cellulose, povidone), disintegrating s (e.g. cornstarch, potato starch, alginic acid, silicon dioxide, croscarmelose sodium, crospovidone, guar gum, sodium starch glycolate), buffers (e.g., Tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizers (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing s (e.g. carbomer, colloidal silicon dioxide, ethyl cellulose, guar gum), sweetners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming s (e.g. ethyl cellulose, acrylates, polymethacrylates) and/or adjuvants.

In one embodiment, the pharmaceutical compositions provided herein are controlled release compositions, i.e. compositions in which the HDAC inhibitor is released over a period of time after administration. Controlled or sustained release compositions include formulation in lipophilic depots (e.g. fatty acids, waxes, oils). In another embodiment, the composition is an immediate release composition, i.e. a composition in which all of the HDAC inhibitor is released immediately after administration.

In another embodiment, the pharmaceutical composition is delivered in a controlled release system. For example, the composition is administered using intravenous infusion, an implantable osmotic pump, a transdermal patch, liposomes, or other modes of administration. In one embodiment, a pump is used (Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (e.g., Goodson, in Medical Applications of Controlled Release, supra, vol. 2, pp. 115-138 (1984). Other controlled release systems are discussed in the review by Langer (Science 249:1527-1533 (1990).

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the HDAC inhibitor or its physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the HDAC inhibitor or its physiologically tolerated derivatives such as salts, esters, N-oxides, and the like are converted into a solution, suspension, or emulsion, if desired with the substances customary and suitable for this purpose, for example, solubilizers or other.

In another embodiment, the active component is formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In another embodiment, the salts of the HDAC inhibitor are pharmaceutically acceptable salts. Other salts are, in one embodiment, useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In one embodiment, the HDAC inhibitor is administered prior to the arrhythmia or arrhythmia-inducing event. In another embodiment, the HDAC inhibitor is administered concomitantly with same. In another embodiment, the HDAC inhibitor is administered after same.

In another embodiment, the HDAC inhibitor is administered within 10 minutes after the arrhythmia or arrhythmia-inducing. In another embodiment, the interval after same is 20 minutes. In another embodiment, the interval is 30 minutes. In another embodiment, the interval is 40 minutes. In another embodiment, the interval is 50 minutes. In another embodiment, the interval is 1 hour. In another embodiment, the interval is 1.5 hours. In another embodiment, the interval is 2 hours. In another embodiment, the interval is 3 hours.

Each time of administration of the HDAC inhibitor represents a separate embodiment of the present invention.

HDAC inhibition assays are well known in the art, and are described, e.g. in Kang J et al (Chem Biol Interact. 2004 Jul. 20; 148(3): 115-23) and in Liu C et al (Methods Mol Biol. 2004; 287: 87-97). Each method of assessing inhibition of HDAC represents a separate embodiment of the present invention.

Thus, novel compounds having utility in treating and reducing the incidence of cardiac rhythm disorders can be used according to the methods of the present invention.

Materials and Experimental Methods

Materials

Trichostatin A was obtained from Sigma-Aldrich.

Histology and Morphology

Hearts were excised from, washed in 37° C. Dulbecco's 1×PBS, arrested in 50 mmol/L KCl, and fixed in 4% formalin. Fixed hearts were cut transversely and sectioned serially from ventricular apex to base. Two sections (5 μm each) were retained at the beginning of each 50-μm step. Sections were stained with Masson's trichrome stain for collagen as a marker of fibrosis. Quantification of the proportion of fibrosis in each heart was then performed with scientific imaging software (Image-J, National Institutes of Health)) and high-resolution serial scanning technique. Histological sections from the entire left ventricle and both atrium were used for analysis from three different hearts.

Electrophysiology Study

An in-vivo electrophysiology study was performed in each mouse to assess atrial and ventricular conduction, refractoriness, and arrhythmia inducibility. Surface ECG recordings and complete in vivo electrophysiological studies (EPS) were obtained from Hop$^{Tg}$ mice (14-18 weeks old), age-matched non-transgenic littermates and TSA-treated Hop$^{Tg}$ mice. Each mouse was anesthetized with pentobarbital (0.033 mg/kg IP), and multi-lead ECGs were obtained using 26-gauge subcutaneous electrodes. Temperature was maintained at 32-33° C. A jugular vein cutdown was performed and an octapolar 2-French electrode catheter (CIBer mouse-EP; NuMED, Inc) placed in the right atrium and ventricle under electrogram guidance to confirm catheter position. A programmed digital stimulator (DTU-215A, Bloom Associates Ltd) was used to deliver electrical impulses at approximately twice diastolic threshold. Surface ECG and intracardiac electrograms were simultaneously displayed on a multichannel oscilloscope recorder (Bard Electrophysiology, Inc) at a digitization rate of 2 kHz and stored on optical media for offline analysis. ECG channels were filtered from 0.5 to 250 Hz and intracardiac electrograms were filtered from 5 to 400 Hz. ECG intervals were measured by two independent observers blinded to the animal's genotype.

ECG Measurements

The PR, QRS, RR, and QT intervals were measured in 6 surface-limb ECG leads by 2 independent observers, who were both blinded to the animals' genotype. Intracardiac recordings were obtained during identical pacing and programmed electrical stimulation protocols for all mice by experienced investigators.

Isolation of Adult Atrial Myocytes

Mice were heparinized, anesthetized with pentobarbital 0.033 milligram [mg]/kilogram [kg] and hearts excised through a sternotomy. Hearts were mounted on a Langendorf apparatus, perfused with Tyrode's solution (composition as in Ref. 21) at 3.0-3.5 milliliter [ml]/minute [min] at a temperature of 36°-37° C. Hearts were perfused with $Ca^{2+}$-free Tyrode's solution for 6 min., followed by 12-15 min. of perfusion with $Ca^{2+}$-free Tyrode's solution containing: collagenase B, collagenase D (Roche Chemical Co.) and protease (Fraction IV, Sigma Chemical Co.). When the hearts appeared pale and flaccid they were removed from the Langendorf apparatus, the atria were dissected away and kept in $Ca^{2+}$-free Tyrode's solution with 1 mg/ml of bovine serum albumin (Fraction XIV, Sigma Chemical Co.). Sections of atrial tissue were then triturated gently with a Pasteur pipette to dissociate individual myocytes.

Quantitative Confocal Immunodetection of Atrial Connexins

The area of immunoreactive signal in discrete spots from isolated atrial myocytes was quantified using laser scanning confocal microscopy. Scanning of single optical slices (<1 μm) by confocal laser scanning microscopy was done on the Leica TCS SP2 system using the spectral detection set for simultaneous fluorescence imaging of Alexa488 and DIC imaging with transmitted light to obtain the cell outline. Sections were acquired through ten randomly selected cells from each group (WT, Hop$^{Tg}$ and TSA-Hop$^{Tg}$) using the 40×, 1.25 NA oil immersion objective at zoom factors ranging from 2 to 3. Areas were quantified using the count nuclei application in the Metamorph software package (Molecular Devices). The total area of each atrial myocyte was calculated from the DIC images and the area of the connexin immunoreactive spots was calculated from the Alexa488 fluorescent images.

Lysis of Atrial Myocytes and Histone Isolation

Isolated atrial myocytes were lysed in Triton X/deoxycholate buffer (20 millimolar [mM] HEPES, pH 7.2, 1% Triton X-100, 1% sodium deoxycholate, 100 mM sodium chloride, 50 mM sodium fluoride, 5 mM EDTA, 100 □M sodium molybdate, with protease inhibitors), and insoluble material was removed by a 15 minute (min) centrifugation in a microfuge, and the supernatant was subjected to 100,000×g, 30 min centrifugation. The pellet was extracted with 9 molar urea, and the resulting pellet extracted with 0.3 molar HCl.

Electrophoresis and Western Blotting

Adult mouse atrium and ventricle were dissected and homogenized in buffer containing 1% Igepal surfactant, 0.5% deoxycholate sodium, 2% SDS, 5 mmol EDTA (pH=7.4), 1% protease inhibitor cocktail tablet (Roche) with and without phosphatase inhibitor cocktail (Sigma-Aldrich). Samples were cleared of debris by centrifugation at 5000 g for 10 min. and the protein concentration was determined using a BCA protein assay kit (Pierce). Protein samples were run on a 4-12% gradient pre-cast SDS-PAGE gel (Invitrogen), and after electrophoresis were transferred onto PVDF membranes (Millipore) using 0.1% acetic acid/10% methanol as a transfer buffer. Membranes were incubated with primary antibodies in 5% milk and PBS overnight at 4° C. and then washed for 5 min, 4 times with TBS-T solution. The following primary antibodies were all used at a concentration of 1:1000 and consisted of: mouse anti-GAPDH monoclonal antibody (Chemicon), mouse anti-TGFβ1 monoclonal antibody (Sigma), rabbit anti-phospho-ERK1/2 polyclonal antibody (Cell Signaling), mouse anti-phospho-JNK monoclonal antibody (Santa Cruz), rabbit anti-phospho-p38-MAPK polyclonal antibody (Santa Cruz), goat anti-IL-1β polyclonal antibody (Santa Cruz), goat anti-connexin40 polyclonal antibody (Santa Cruz), rabbit anti-connexin43 polyclonal antibody (Zymed) and anti-acetyl H3 antibody (Upstate Charlottesville, Va.) which recognizes acetyl-Lys9H3 peptides. Membranes were then incubated with secondary antibody (1:250, Western Breeze, Invitrogen) for 45 min. at room temperature and subsequently washed in TBS-T for 5 min. 4 times. Results were visualized by enhanced chemiluminescence using a commercially available kit (Western Breeze, Invitrogen) and data were recorded on BioMax-MR film (Kodak, Rochester, N.Y.). Densitometry was determined using the Image-J software package (National Institutes of Health).

Enzyme-Linked Immunosorbent Assay

Whole hearts were suspended in 1 molar acetic acid, homogenized and centrifuged at 15,000×g for 30 minutes at 4° C. Supernatants were dried, reconstituted with 0.1% trifluoroacetic acid and purified on a C18 Sep-Pak column (Waters Associates). This fraction was eluted from the column with 30% acetonitrile in 5 mL of 0.1% trifluoroacetic acid, dried and dissolved in 0.25 mL Tris-buffered saline plus 0.1% Tween 80 (TBST) solution. Protein concentration was determined by the Bradford method and 200 µg samples were analyzed in a microtiter plate using an anti-angiotensin II antibody (Peninsula ELISA) and biotinylated angiotensin II as a tracer. The microtiter plate was washed 5 times with TBST and treated with streptavidin-horseradish peroxidase. The color reaction was developed with 100 µL of tetramethylbenzidine substrate and terminated by addition of 2 normal HCl. The absorbance was recorded at 450 nanometers and angiotensin II concentration was calculated from the standard curve generated each time.

Invasive Hemodynamic Measurements

Hop$^{Tg}$ mice 14-18 weeks old were compared with wild-type littermates and TSA treated Hop$^{Tg}$ mice. Anesthesia was induced with 3% isoflurane and maintained by ventilation with 0.75% isoflurane. Temperature was maintained at 36-37° C. Intracardiac pressures were recorded using a 1.4 French micromanometer catheter (Micro-Tip SPR-671; Millar Instruments) that was zeroed prior to making measurements on each animal in a saline bath. The catheter was inserted via the right carotid artery to record intracardiac pressures and digitized at 2-kHz using a PowerLab/16 SP A/D converter (ADInstruments Ltd.).

Statistical Analyses

All continuous variables, were compared with those of sex- and age-matched control mice, with data presented as the mean±SD. Continuous variables, such as ECG intervals, cardiac conduction properties, intracardiac pressures and area of fibrosis were compared by two-way ANOVA using a commercially available statistical software package (SPSS 12.0). Test of significance between groups was performed using Bonferroni's multiple comparisons tests. The numbers of arrhythmic episodes were assumed to have a Poisson distribution and the Kolmogorov-Smirnov test was used to assess statistical significance between groups. A value of P<0.05 was considered statistically significant.

Example 1: Trichostatin A Reverses Inducible Atrial Arrhythmia

Trichostatin A 0.6 mg/kg daily in a volume of 0.2 mL was given by intraperitoneal injection for 14 consecutive days prior to cardiac electrical stimulation in Hop transgenic mice (Hop$^{Tg}$) compared with wild-type controls (WT).

Invasive electrophysiology studies revealed Hop$^{Tg}$ mice had significantly more and longer episodes of inducible atrial fibrillation than trichostatin A treated Hop$^{Tg}$ or control mice. Trichostatin A treatment of Hop$^{Tg}$ mice reduced the duration and episodes of atrial fibrillation, atrial fibrosis and restored the distribution of connexin40 and connexin43 in the atrium.

Table 1 shows the results of invasive cardiac electrical stimulation in Hop transgenic mice (Hop$^{Tg}$) compared with wild-type controls (WT), while treatment with trichostatin A of Hop transgenic mice (TSA-Hop) resulted in complete reversal of atrial arrhythmia inducibility. Atrial programmed electrical stimulation induced significantly more and longer episodes of atrial arrhythmia in 9 of 11 Hop$^{Tg}$ mice compared to control littermates where atrial arrhythmias were induced in 2 of 12 mice (P<0.01). Ventricular programmed electrical stimulation induced similar numbers and durations of ventricular tachycardia in 3 of 11 Hop$^{Tg}$ mice compared to 4 of 12 control mice (P=NS). Following treatment with trichostatin A from a separate cohort of Hop$^{Tg}$ mice (TSA-Hop$^{Tg}$) atrial programmed electrical stimulation induced significantly fewer and shorter episodes of atrial arrhythmia in only 2 of 10 TSA-Hop$^{Tg}$ mice compared to the Hop$^{Tg}$ mice (P<0.01). Similarly, ventricular programmed electrical stimulation also induced fewer and shorter episodes of ventricular tachycardia in 2 of 10 TSA-Hop$^{Tg}$ mice compared to Hop$^{Tg}$ mice (P<0.05). *P<0.05 compared to WT; †P<0.05 compared to TSA-Hop$^{Tg}$.

TABLE 1

Summary of Inducible Arrhythmias in Hop Transgenic Mice.

|  | Hop$^{Tg}$ (n = 11) | WT (n = 12) | TSA-Hop$^{Tg}$ (n = 10) |
|---|---|---|---|
| Episodes AT | 48*† | 9 | 5 |
| Duration AT (s) | 1.307 ± 0.289*† | 0.167 ± 0.114 | 0.148 ± 0.110 |
| AT CL (ms) | 46.2 ± 10.0 | 45.4 ± 5.5 | 47.0 ± 7.2 |
| Mice with AT | 13/15*† | 2/15 | 2/15 |
| Episodes VT | 11† | 10† | 4 |
| Duration VT (s) | 3.31 ± 3.08 | 2.77 ± 1.69 | 0.89 ± 1.07 |
| VT CL (ms) | 50.7 ± 9.9 | 51.5 ± 7.8 | 50.4 ± 8.6 |
| Mice with VT | 3/15 | 4/15 | 2/15 |

AT = Atrial tachycardia;
AT CL = atrial tachycardia cycle length;
VT = Ventricular tachycardia;
VT CL = ventricular tachycardia cycle length.

Example 2: Trichostatin A Has Minimal Effects Upon Cardiac Structure and Function in Hop Transgenic Mice Trichostatin A 0.6 mg/kg daily in a volume of 0.2 mL was given by intraperitoneal injection for 14 consecutive days upon inducible atrial arrhythmias and atrial structurally remodeling in an engineered mouse model with left ventricular hypertrophy and inducible atrial fibrillation. Transgenic mice over-expressing the homeodomain-only protein (Hop$^{Tg}$), which promotes cardiac hypertrophy and interstitial fibrosis, were divided into three groups: control, Hop$^{Tg}$ mice and Hop$^{Tg}$ mice treated with trichostatin A.

Table 2 shows the results of invasive hemodynamics measurements and morphometeric analysis of hearts from Hop transgenic mice (Hop$^{Tg}$) compared with wild-type controls (WT) and Hop transgenic mice treated with trichostatin A (TSA-Hop). Hop$^{Tg}$ mice had higher left ventricular end-diastolic pressure (LVEDP), and reduced peak systolic contraction and diastolic relaxation compared to WT mice. However, trichostatin A had no effect upon the LVEDP, systolic contraction or diastolic relaxation when treatment was initiated in animals aged 12-14 weeks of age. These parameters were similar between Hop$^{Tg}$ and TSA-Hop$^{Tg}$ mice, though still abnormal when compared to WT mice. In addition, the heart weight to tibia length ratio (HW/TL) was higher in Hop$^{Tg}$ and TSA-Hop$^{Tg}$ mice compared to WT, but there was no difference in the HW/TL between Hop$^{Tg}$ and TSA-Hop$^{Tg}$ mice. *P<0.05 compared to WT; †P<0.05 compared to TSA-Hop$^{Tg}$.

TABLE 2

Invasive Hemodynamic and Morphometric Parameters in Hop Transgenic Mice.

|  | Hop$^{Tg}$ (n = 8) | WT (n = 9) | TSA-Hop$^{Tg}$ (n = 8) |
|---|---|---|---|
| Heart rate (bpm) | 378 ± 50.4 | 407 ± 61.2 | 392 ± 63.5 |
| LV systolic pressure (mmHg) | 94.6 ± 12.4 | 90.9 ± 15.8 | 90.6 ± 8.8 |
| LV end diastolic pressure (mmHg) | 7.0 ± 1.6* | 3.9 ± 1.5 | 7.2 ± 2.4* |
| Peak positive dP/dt (mmHg/s) | 7001 ± 2337 | 6815 ± 3434 | 6465 ± 1613 |
| Peak negative dP/dt (mmHg/s) | −2051 ± 1268* | −4060 ± 808 | −2267 ± 1320* |
|  | HopX$^{Tg}$ (n = 11) | WT (n = 15) | TSA-HopX$^{Tg}$ (n = 13) |
| Heart weight (mg) | 201 ± 17.0* | 121.4 ± 11.5 | 192.8 ± 15.5* |
| Heart weight/body weight (mg/g) | 11.0 ± 5.5* | 8.1 ± 6.1 | 7.4 ± 0.67* |

LV = left ventricular.

Figure 1:
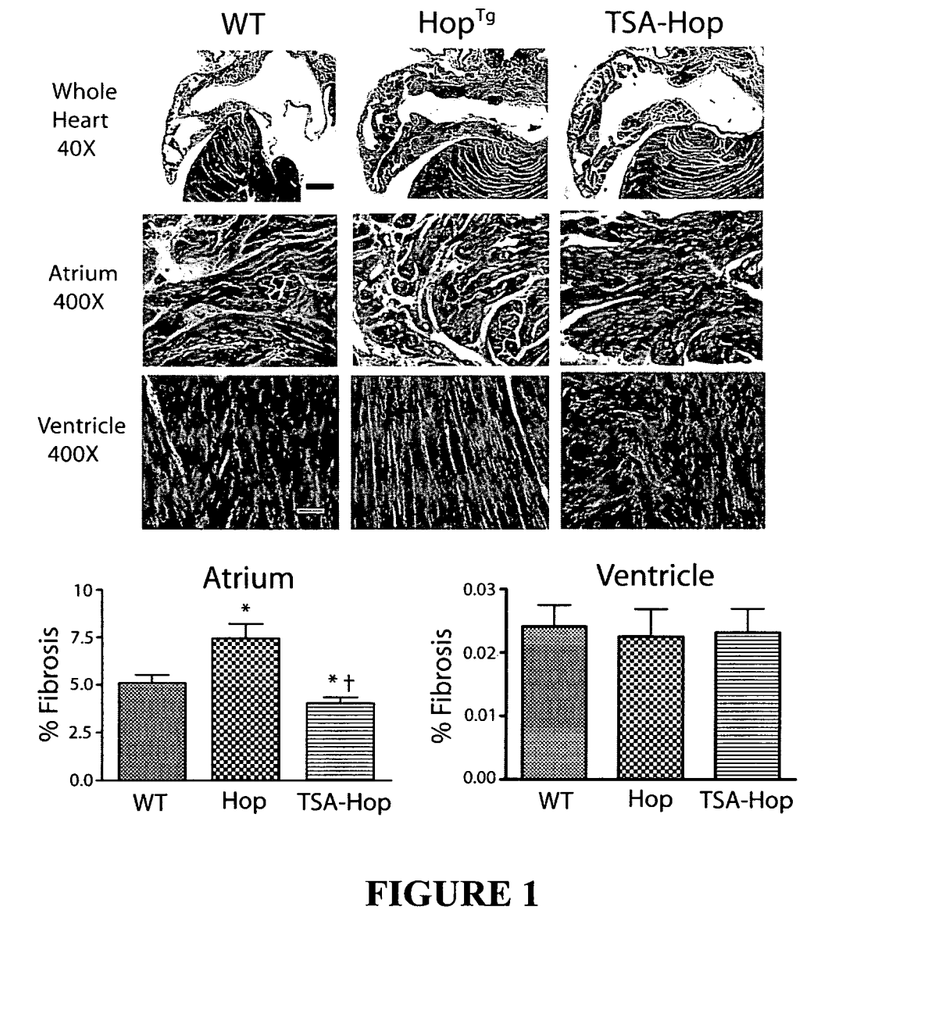

Mason's trichrome staining revealed increased atrial interstitial fibrosis in Hop transgenic mice (Hop$^{Tg}$) compared with wild-type controls (WT), while treatment with trichostatin A of Hop transgenic mice (TSA-Hop) resulted in complete reversal of atrial fibrosis. There was no obvious ventricular interstitial fibrosis in the three groups shown (FIG. 1).

To better characterize the effects of TSA upon ventricular structure and function, echocardiographic analysis of HopX$^{Tg}$, TSA-HopX$^{Tg}$ and WT mice was performed. This analysis revealed that HopX$^{Tg}$ mice do have increased ventricular wall thickness with enhanced ventricular systolic function compare to their WT littermates (Table 4). However, TSA had no effect upon these parameters as ventricular wall thickness and systolic function were similar between HopX$^{Tg}$ and TSA-HopX$^{Tg}$ mice (Table 4), consistent with the hemodynamic analysis of these animals.

TABLE 3 shows the effects of TSA upon ventricular function in Hop mice as assessed by echocardiography.

|  | HopX$^{Tg}$ (n = 4) | WT (n = 4) | TSA-HopX$^{Tg}$ (n = 4) |
|---|---|---|---|
| Left Ventricle Posterior Wall (mm) | 1.18 ± 0.26* | 0.69 ± 0.07 | 1.10 ± 0.14* |
| Intra-ventricle Septum (mm) | 1.2 ± 0.24* | 0.71 ± 0.05 | 1.13 ± 0.18* |

TABLE 3-continued shows the effects of TSA upon ventricular function in Hop mice as assessed by echocardiography.

|  | HopX$^{Tg}$ (n = 4) | WT (n = 4) | TSA-HopX$^{Tg}$ (n = 4) |
|---|---|---|---|
| LV Fractional Shortening (%) | 59.9 ± 15.3* | 31.50 ± 3.31 | 53.9 ± 0.50* |
| LV Ejection Fraction (%) | 87.9 ± 13.0* | 59.3 ± 3.51* | 87.7 ± 7.00* |

*$P < 0.05$ compared to WT;
†$P < 0.05$ compared to TSA-HopX$^{Tg}$.
LV = left ventricular.

Example 3: Levels of Cardiac Angiotensin Remain Unchanged in Hop and Control Mice Trichostatin A 0.6 mg/kg daily in a volume of 0.2 mL was given by intraperitoneal injection for 14 days upon inducible atrial arrhythmias and atrial structurally remodeling in an engineered mouse model with left ventricular hypertrophy and inducible atrial fibrillation. Transgenic mice over-expressing the homeodomain-only protein (Hop$^{Tg}$), which promotes cardiac hypertrophy and interstitial fibrosis, were divided into three groups: control, Hop$^{Tg}$ mice and Hop$^{Tg}$ mice treated with trichostatin A.

Figure 2:
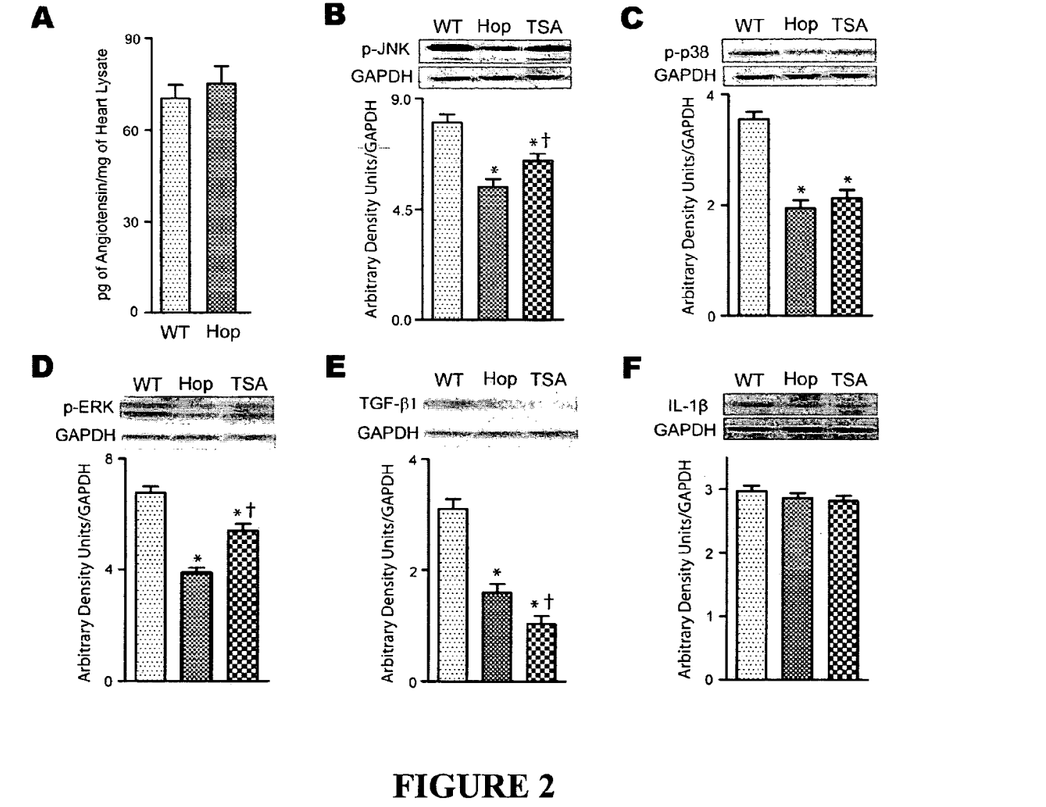
FIG. 2 depicts bar graphs representing the levels of cardiac angiotensin and atrial cytokines after over-expression of Hop in the heart.

Enzyme-linked immunosorbent assay showed that myocardial angiotensin II levels were similar between control and Hop$^{Tg}$ mice, suggesting the effects of trichostatin A are independent of angiotensin II (FIG. 2A). These results suggest that histone-deacetylase inhibition reverses atrial substrate remodeling and atrial fibrillation vulnerability in an intact in vivo mouse model of left ventricular hypertrophy. Furthermore, the levels of atrial cytokines were assessed in Western blot analysis in mice over-expressing Hop in the heart and WT, control, mice (FIGS. 2B-F). Specifically, FIG. 2B-F shows the relative protein expression of the activated form of several mitogen-activated protein kinases and cytokines and in the atrium of Hop transgenic mice (Hop$^{Tg}$) compared with wild-type controls (WT) and Hop transgenic mice treated with trichostatin A (TSA-Hop). Activated TGF-β1 is lower in Hop$^{Tg}$ mice relative to control and further decreased in TSA-Hop$^{Tg}$ mice. Phospho-ERK1/2 is also lower in Hop$^{Tg}$ mice relative to control but increased in TSA-Hop$^{Tg}$ mice. Phospho-JNK and phospho-p38-MAPK were not different between Hop$^{Tg}$, TSA-Hop$^{Tg}$ or control mice.

Example 4: Connexin40 and Connexin43 Expression in Hop Transgenic Mice

Trichostatin A 0.6 mg/kg daily in a volume of 0.2 mL was given by intraperitoneal injection for 14 days upon inducible atrial arrhythmias and atrial structurally remodeling in an engineered mouse model with left ventricular hypertrophy and inducible atrial fibrillation. Transgenic mice over-expressing the homeodomain-only protein (Hop$^{Tg}$), which promotes cardiac hypertrophy and interstitial fibrosis, were divided into three groups: control, Hop$^{Tg}$ mice and Hop$^{Tg}$ mice treated with trichostatin A.

Figure 3:
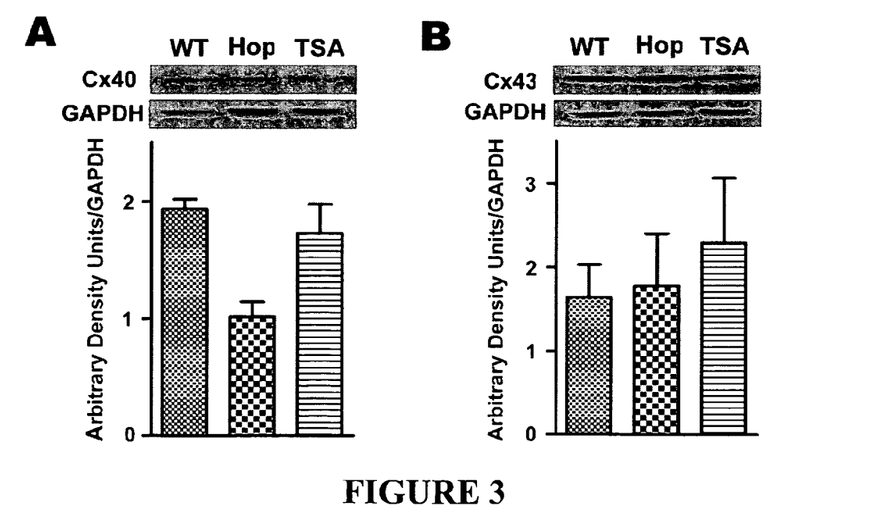
FIG. 3 depicts bar graphs representing connexin40 expression in left Hop transgenic mice and normalized by trichostatin A (TSA).

Connexin40 expression was reduced with left ventricular hypertrophy in Hop transgenic mice and normalized by trichostatin A. FIG. 3A shows an immunoblot analysis of atrial connexin40 which was found to be lower in Hop$^{Tg}$ mice and normalized by TSA. FIG. 3B shows that no changes in connexin43 expression were evident between wild-type (WT), Hop transgenic (Hop) and trichostatin A treated Hop transgenic mice (TSA-Hop).

Example 5: Testing of Compounds for Inhibition of HDAC Activity in Cardiac Myocyte Extracts HDAC activity of cardiac myocyte extracts are assessed, in the presence and absence of a test compound.

This assay is used to identify novel agents to treat and reduce cardiac arrhythmia, as inhibition of HDAC activity is in the present invention leads to reduction in cardiac arrhythmia.

Example 6: Effects of TSA Upon Atrial Weight to Body Weight and Tibia Length With regards to mechanical function, TSA has been shown to improve myocardial mechanical function in models of pressure-overload and angiotensin-induced hypertrophy. Therefore, it is possible that TSA reduces atrial arrhythmogenesis by improving myocardial mechanical function and normalizing intracardiac pressures. However, no significant changes were observed in the HW/TL, AW/TL, LVEDP, peak positive dP/dt or peak negative dP/dt in HopX$^{Tg}$ mice treated with TSA compared to HopX$^{Tg}$ mice without TSA treatment.

Echocardiographic, MRI and histological analysis did not reveal any evidence of mitral valve abnormalities in HopX$^{Tg}$ mice, so the LVEDP accurately reflects left atrial pressure. While TSA treatment partially reduces cardiac hypertrophy in 3 week-old HopX$^{Tg}$ mice, this does not appear to be the case in the older 14-18 week-old mice used in the examples described herein since no change were observed in the heart weight/tibial length ratio, atrial weight/tibial length ratio or left ventricular wall dimensions. While myocardial dysfunction and altered hemodynamics probably do contribute to atrial arrhythmogenesis in this model, it appears HDACi does not target these factors in reversing atrial fibrosis and arrhythmias.

The apparent discrepancy observed in the effects of HDACi upon cardiac hypertrophy in 14-18 week-old HopX$^{Tg}$ mice, compared to its effect in models of hypertrophy induced by pressure-overload or angiotensin-infusion, are related to differences in the downstream pathways evoked by HopX over-expression. Specifically, cardiac restricted over-expression of HopX does not affect myocardial angiotensin II, and this may be another pathway HDACi affects but is not active in this model. A relatively low dose of TSA was selected in this example (0.6 mg/kg/day) for a short treatment period (2 weeks) to see if is possible to selectively target atrial pathology and arrhythmogenesis, without inducing significant effects upon ventricular function or morphology. This turned out to be the case in this model, and previous studies have shown that TSA used at a dosage of 0.6 mg/kg/day does augment histone acetylation in the heart. In addition, it is possible once cardiac hypertrophy is established, and temporally removed from the embryonic gene programs responsible for its development, HDAC inhibition will no longer have significant effects upon regression of hypertrophy. Class I HDACs also complex with and regulate the function of non-histone proteins, in particular transcription factors through alterations in acetylation. The dramatic reversal of established atrial structural changes and fibrosis observed in this model indicates these effects of HDAC inhibition are less dependent upon global alterations in transcription induced by chromatin winding/relaxation, and are related to regulation of specific transcription factors involved with fibrosis and inflammation, such as Sp1 and p65.

What is claimed is:

1. A method of treating a cardiac rhythm disorder in a subject having a cardiac rhythm disorder, comprising administering to said subject a pharmaceutical composition consisting of:
   (i) an active ingredient consisting of a therapeutically effective amount of an inhibitor of a histone deacetylase (HDAC) to alleviate the cardiac rhythm disorder; and
   (ii) one or more pharmaceutically acceptable excipients wherein the cardiac rhythm disorder is atrial fibrillation, and wherein the HDAC is a class I, II, or IV HDAC.

2. The method of claim 1, wherein said inhibitor of an HDAC is trichostatin A.

3. The method of claim 1, wherein said inhibitor of an HDAC is selected from: a valproic acid, a suberoylanilide hydroxamic acid (SAHA), an epoxyketone-containing cyclic tetrapeptide, a non-epoxyketone-containing cyclic tetrapeptide, a benzamine, depudecin, or any mixture thereof.

4. The method of claim 1, wherein the step of treating a cardiac rhythm disorder in said subject, comprises restoring atrial connexin distribution in said subject.

5. The method of claim 1, wherein the step of administering comprises administering said HDAC inhibitor in a therapeutically effective amount to reduce atrial collagen content in said subject.

6. A method of treating an atrial fibrillation disorder in a subject having atrial fibrillation consisting essentially of administering to said subject a pharmaceutical composition consisting of:
   (i) an active ingredient consisting of a therapeutically effective amount of an inhibitor of a histone deacetylase (HDAC) to alleviate the atrial fibrillation, wherein the HDAC is a class I, II, or IV HDAC, and
   (ii) one or more pharmaceutically acceptable excipients.

7. The method of claim 6, wherein the HDAC inhibitor is formulated for oral administration.

8. The method of claim 6, wherein the HDAC inhibitor is formulated for parenteral administration.

9. The method of claim 6, wherein the HDAC inhibitor is suberoylanilide hydroxamic acid (SAHA).

10. The method of claim 1, wherein the HDAC inhibitor is suberoylanilide hydroxamic acid (SAHA).

* * * * *